United States Patent [19]

Hajos et al.

[11] 4,307,019

[45] Dec. 22, 1981

[54] TOTAL SYNTHESIS OF 1RS,4SR,5RS,-4-(4,8-DIMETHYL-5-HYDROXY-7-NONEN-1-YL)-4-METHYL-3,8-DIOXABICYCLO[3.2.1]OCTANE-1-ACETIC ACID

[75] Inventors: Zoltan G. Hajos, Princeton; Seymour Levine, North Brunswick, both of N.J.

[73] Assignee: Ortho Pharmaceutical Corporation, Raritan, N.J.

[21] Appl. No.: 219,563

[22] Filed: Dec. 23, 1980

Related U.S. Application Data

[62] Division of Ser. No. 181,308, Aug. 25, 1980.

[51] Int. Cl.³ .............................................. C07D 319/10
[52] U.S. Cl. .................................................... 260/340.6
[58] Field of Search ..................................... 260/340.6

[56] References Cited

U.S. PATENT DOCUMENTS

| | | | |
|---|---|---|---|
| 4,102,895 | 7/1978 | Kanojia et al. | 260/340.6 |
| 4,215,048 | 7/1980 | Chen et al. | 260/340.6 |
| 4,237,054 | 12/1980 | Chen | 260/340.6 |
| 4,237,055 | 12/1980 | Hajos et al. | 260/340.6 |

*Primary Examiner*—Ethel G. Love
*Attorney, Agent, or Firm*—Benjamin F. Lambert

[57] ABSTRACT

The synthesis of 1RS,4SR,5RS-4-(4,8-dimethyl-5-hydroxy-7-nonen-1-yl)-4-methyl-3,8-dioxabicyclo[3.2.1]octane-1-acetic acid is described. The bicyclo acetic acid compound is useful as a uteroevacuant agent.

7 Claims, No Drawings

TOTAL SYNTHESIS OF 1RS,4SR,5RS,-4-(4,8-DIMETHYL-5-HYDROXY-7-NONEN-1-yl)-4-METHYL-3,8-DIOXABICY-CLO[3.2.1]OCTANE-1-ACETIC ACID

This is a division of application Ser. No. 181,308, filed Aug. 25, 1980.

The isolation and structure determination of zoapatanol, 2S,3R,6E-(2″-hydroxyethylidene)-2-methyl-2-(4′,8′-dimethyl-5′-oxo-7′-nonenyl)-oxepan-3-ol, one of the active ingredients in the zoapatle plant, is described in U.S. Pat. No. 4,086,358, issued Apr. 25, 1978. In U.S. Pat. No. 4,102,895, issued July 25, 1978, the preparation of 1R,4S,5R-4-(4,8-dimethyl-5-hydroxy-7-nonen-1-yl)-4-methyl-3,8-dioxabicyclo[3.2.1]octane-1-acetic acid, a compound derived from zoapatanol, is described. The bicyclic derivative has the following formula:

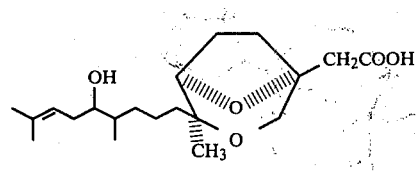

The present invention relates to a method of synthesizing the racemic 1RS,4SR,5RS-4-(4,8-dimethyl-5-hydroxy-7-nonen-1-yl)-4-methyl-3,8-dioxabicyclo [3.2.-1]octane-1-acetic acid. This acetic acid derivative is active as a utero-evacuant agent. Many of the intermediates employed in the synthesis are novel compounds and are included as part of the invention.

The synthesis is comprised of several steps which are summarized in the following schematic diagram:

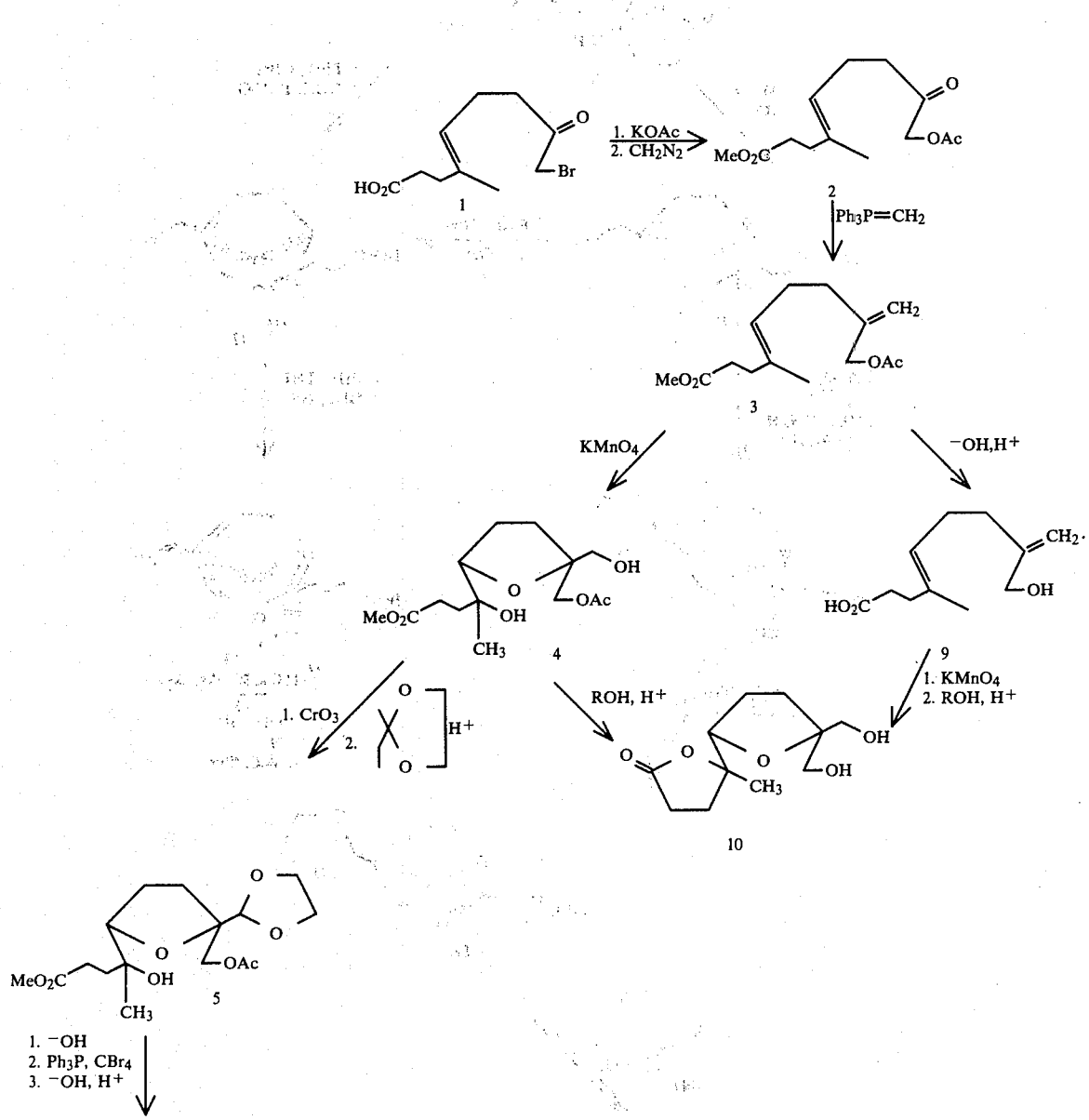

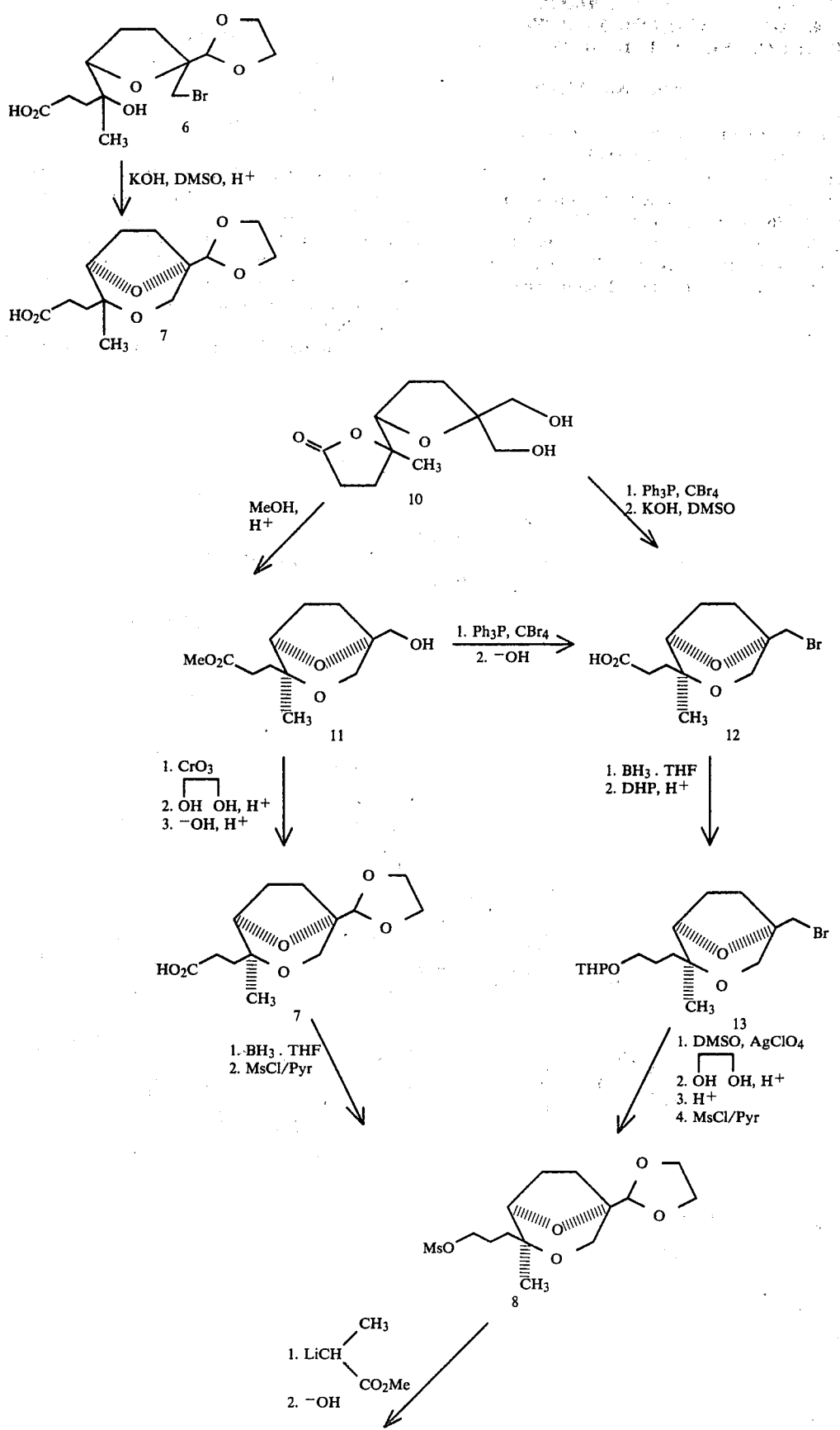

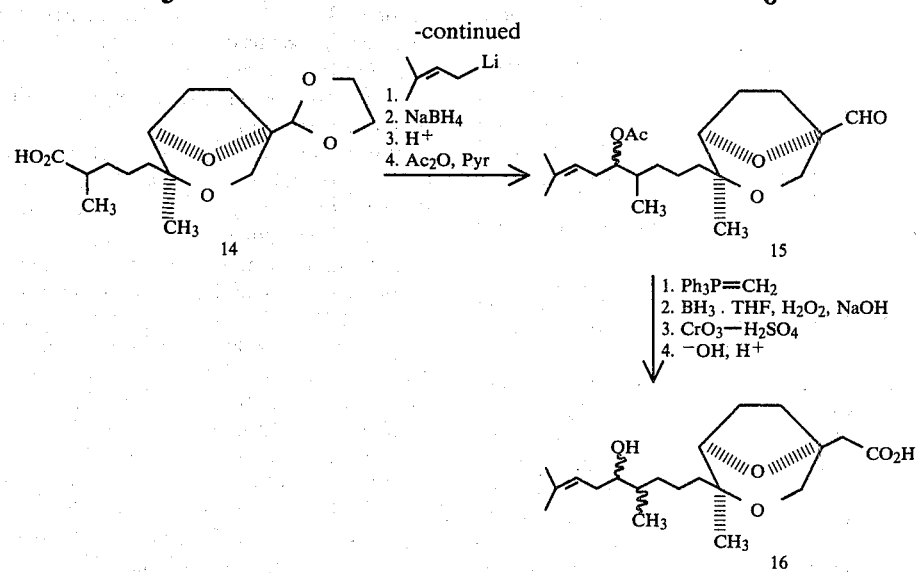

wherein Ph is a phenyl group, Ac is an acetyl group, THP is a tetrahydropyranyl group, Ms is a mesyl group, R is methyl or ethyl, DMSO is dimethylsulfoxide and DHP is dihydropyran.

As can be seen from the diagram, the first step in the synthesis involves the preparation of a keto ester (2) which is prepared by reacting a bromo keto acid (1) first with potassium acetate in a suitable solvent such as acetone. The acetoxy keto acid which forms is then reacted with diazomethane to form the keto ester (2). The reaction is carried out in a suitable solvent such as ether at a temperature between −10°–15° C. The preferred reaction temperature is about 0° C. The keto ester (2) is then converted to a methylene ester (3) by reaction with methyltriphenylphosphoniumylide in a suitable solvent such as tetrahydrofuran, dimethylsulfoxide and benzene. The methyltriphenylphosphoniumylide compound is prepared by reacting methyltriphenylphosphonium bromide with n-butyllithium in a suitable solvent such as hexane. The methylene ester (3) is then hydrolyzed to the corresponding hydroxy acid (9) by treatment with a strong aqueous base such as sodium hydroxide. The hydroxy acid is first oxidized and then cyclized in an acidic solution to form a tetrahydrofuranyl-γ-lactone (10). Aqueous potassium permanganate can be employed as the oxidizing agent. Suitable solvents for the reaction include acetone, dioxane and 2-butanone. Acids which can be employed for the cyclization step include conc. sulfuric acid, phosphoric acid and hydrochloric acid. Solvents which can be employed include methanol, ethanol and dioxane.

The tetrahydrofuranyl-γ-lactone compound (10) is converted to the 3-methanesulfonyloxypropyl-3,8-dioxabicyclo-octane derivative (8) in six steps. The first step involves the conversion of the tetrahydrofuranyl-8-lactone compound (10) to the bicyclic hydroxy ester (11) by reaction with a strong acid such as conc. sulfuric acid in a suitable solvent such as methanol. The reaction can be carried out at a temperature between room temperature and 70° C. The preferred reaction temperature is about 55° C. In the second step the bicyclic hydroxy ester (11) is converted to the corresponding dioxolan dioxabicyclo-octane carboxylic acid (7) by first reacting it with an oxidizing agent such as Jones reagent. The oxidation may be carried out at a temperature between 0° C. and room temperature in a suitable solvent such as acetone. The preferred reaction temperature is about 0° C. The oxidation product is then reacted with ethylene glycol in the presence of an acid such as p-toluenesulfonic acid. Solvents which can be employed include benzene and toluene. The reaction is preferably carried out at the reflux temperature of the solvent. The 1,3-dioxolan ester is then hydrolyzed with base such as sodium hydroxide and the 3,8-dioxabicyclo octane derivative (7) is obtained from the reaction mixture by techniques known to those skilled in the art. The 3,8-dioxabicyclo octane (7) is then converted to the corresponding mesylate (8) by first reacting it with borane tetrahydrofuran. The reaction can be carried out at a temperature between 0° C. and room temperature. The preferred reaction temperature, however, is about 0° C. The intermediate compound is then treated with methanesulfonyl chloride in a suitable solvent such as methylene chloride, for example, in the presence of a base such as pyridine or triethylamine. The reaction can be carried out at a temperature between 0° C. and room temperature. The preferred reaction temperature is about 0° C. Solvents which can be employed include methylene chloride chloroform.

Alternatively, the dioxabicyclo octane derivative (7) can be prepared from the methylene ester (3) by a different synthetic route, the first step of which involves the cyclization of the ester to the corresponding tetrahydrofuranyl diester (4) by oxidation with a suitable oxidizing agent such as, for example, aqueous potassium permanganate. (The tetrahydrofuranyl diester (4) can be converted to the tetrahydrofuranyl-γ-lactone compound (10) by reaction with strong acid such as, for example, concentrated sulfuric acid in a suitable solvent such as methanol.)

The hydroxy group in the tetrahydrofuranyl diester (4) is converted to the corresponding dioxolan diester (5) in two steps. The first step involves oxidation to the aldehydic precursor with a suitable oxidizing agent such as chromium trioxide/pyridine, for example. The aldehyde is then treated with methyl ethyl ketone cyclic ethylene ketal in the presence of an acid to form the dioxolan diester (5). The reaction is carried out in a suitable solvent such as benzene or toluene. Acids which can be employed include p-toluenesulfonic acid and camphorsulfonic acid.

The dioxolan diester (5) is converted to the corresponding dioxolan bromo acid (6) in three steps. In the first step the dioxolan diester (5) is converted to a dihydroxy acid by hydrolysis with aqueous base such as, for example, aqueous sodium hydroxide. The dihydroxy acid is then dissolved in carbon tetrabromide and the solution is treated with triphenylphosphine followed by treatment with aqueous base such as sodium bicarbonate, for example, to hydrolyze the intermediate acyl halide. The dioxolan bromo acid (6) is obtained from the reaction mixture by techniques known to those skilled in the art.

The dioxolan bromo acid (6) is converted to the corresponding dioxabicyclo octane derivative (7) by reaction with a base such as potassium hydroxide in a suitable solvent such as dimethylsulfoxide. The reaction can be carried out at a temperature between room temperature and 60° C. The preferred temperature is about 45° C. The dioxolan bromo acid is obtained from the reaction mixture by techniques known to those skilled in the art.

Alternatively the mesylate (8) can be prepared by reacting the tetrahydrofuranyl-γ-lactone derivative (10) with carbon tetrabromide and triphenylphosphine in a suitable solvent such as methylene chloride to form the corresponding bis-bromomethyl derivative which is reacted with a base such as potassium hydroxide in a suitable solvent such as dimethylsulfoxide followed by acidification with a suitable acid such as hydrochloric acid to form the bromomethyl dioxabicyclo-octane carboxylic acid (12). The acid is converted to the tetrahydropyran-2-yloxy propyl derivative by first reacting it with borane in tetrahydrofuran. The 3-hydroxy-3,8-dioxabicyclo octane intermediate is then converted into the 3-tetrahydropyranyl-3,8-dioxabicyclo derivative (13) by reaction with dihydropyran in the presence of an acid such as p-toluenesulfonic acid. Solvents which can be employed include ether, tetrahydrofuran and dioxane. The 3-tetrahydropyranyl-3,8-dioxabicyclo octane is then converted to the 3-methanesulfonyloxypropyl-3,8-dioxabicyclo octane derivative (8) by first reacting it with silver perchlorate in a suitable solvent such as dimethylsulfoxide. The 1-formyl intermediate which forms is then reacted with ethylene glycol in the presence of an acid such as p-toluenesulfonic acid, for example. Suitable solvents which can be employed include benzene and toluene. The reaction is preferably carried out at the reflux temperature of the solvent. The 1-(1,3-dioxolan) intermediate is then hydrolyzed with an acid such as aqueous hydrochloric acid or p-toluenesulfonic acid and the 4-(3-methanesulfonyloxypropyl) compound (8) is formed by reacting the 4-(3-hydroxypropyl) intermediate with methanesulfonyl chloride as described above. The bromomethyl dioxabicyclo-octane carboxylic acid (12) can also be prepared from the hydroxy ester octane (11) by reaction with carbon tetrabromide and triphenylphosine in a suitable solvent such as tetrahydrofuran followed by treatment with an alkali metal hydroxide such as sodium hydroxide in a suitable solvent such as methanol or aqueous sodium bicarbonate.

The 4-(3-methanesulfonyloxypropyl) compound (8) is converted to the 4-(4-carboxypentyl) derivative (14) by reaction first with methyl-2-lithio-propionate in a suitable solvent such as tetrahydrofuran and followed by hydrolysis with a base such as aqueous sodium hydroxide. The displacement reaction is carried out at a temperature between −20° and −100° C. The preferred reaction temperature is about −78° C.

The 4-(4-carboxypentyl) compound (14) is then converted to the 4-(5-acetoxy-4,8-dimethyl-7-nonenyl)-4-methyl-1-oxomethyl-3,8-dioxabicyclo[3.2.1]octane (15) by first reacting it with 3-methyl-2-butenyl lithium in the presence of lithium hydride in a suitable solvent such as ether dimethoxyethane and tetrahydrofuran. The 5-oxo intermediate is then reacted with sodium borohydride in a suitable solvent such as methanol and the resulting 5-hydroxy compound is treated with an acid such as, aqueous hydrochloric acid and p-toluenesulfonic acid, for example, in a solvent such as acetone to hydrolyze the acetal. The resulting 5-hydroxy aldehyde is then esterified with an esterifying agent such as acetic anhydride or acetyl chloride.

The 4-(5-acetoxy-4,8-dimethyl-7-nonenyl)-4-methyl-1-oxomethyl-3,8-dioxabicyclo[3.2.1]octane (15) is then converted to 1RS,4SR,5RS-4-(4,8-dimethyl-5-hydroxy-7-nonenyl)-4-methyl-3,8-dioxabicyclo[3.2.1]octane-1-acetic acid in four steps. In the first step, the aldehyde (15) is reacted with an ylide prepared from methyltriphenylphosphonium bromide and n-butyllithium in a suitable solvent such as tetrahydrofuran, dimethylsulfoxide and benzene. The 1-vinyl intermediate is then reacted first with borane in tetrahydrofuran and the reaction mixture is then treated with a base such as sodium hydroxide, for example, followed by hydrogen peroxide. The 1-(2-hydroxyethyl) compound which forms is then treated with Jones reagent (chromium trioxide and sulfuric acid). The free acid is obtained from the reaction mixture by techniques known to those skilled in the art. Conventional hydrolysis of the ester with a base such as sodium hydroxide yields 1RS,4SR,5RS-4-(4,8-dimethyl-5-hydroxy-7-nonenyl)-4-methyl-3,8-dioxabicyclo[3.2.1]octane-1-acetic acid acid (16).

The starting material is the preparation of 1RS,4SR,5RS-4-(4,8-dimethyl-5-hydroxy-7-nonen-1-yl)-4-methyl-3,8-dioxabicyclo[3.2.1]octane-1-acetic acid, i.e., the bromo keto ester (1) is prepared according to the method described in co-pending application Ser. No. 146,538, filed May 2, 1980.

The following examples describe the invention in greater detail and are intended to be a way of illustrating but not limiting the invention.

EXAMPLE 1

Methyl 1-Acetoxy-6-methyl-2-oxo-5(E)-nonen-9-oic acid (2)

A solution of 1-bromo-6-methyl-2-oxo-5(E)-nonen-9-oic acid (13.1 g, 50 mM) in acetone (100 ml) at room temperature under nitrogen is stirred with anh. potassium acetate (10 g, 0.1 M) for 16 hr. The mixture is filtered through Hy-flo and concentrated in vacuo. The residue is dissolved in CHCl$_3$, washed with 8% NaCl—H$_2$O, dried (Na$_2$SO$_4$) and evaporated in vacuo to give an acetoxy keto acid. This is dissolved in anh. diethyl ether (50 ml), and treated at 0° C. under nitrogen with a slight excess of diazomethane in ether for 2 hr. A few drops of methanol are added, and the solvent is evaporated in vacuo. The residue is worked up as above to give methyl 1-acetoxy-6-methyl-2-oxo-5(E)-nonen-9-oic acid.

EXAMPLE 2

Methyl 1-Acetoxy-6-methyl-2-methylene-5(E)-nonen-9-oic acid (3)

A suspension of methyltriphenylphosphonium bromide (21.5 g, 60 mM) in tetrahydrofuran (200 ml) at 0° C. is treated with n-butyllithium in hexane (30 ml, 2 M) and stirred for 1 hr at 0° C. A solution of methyl 1-acetoxy-6-methyl-2-oxo-5(E)-nonen-9-oic acid (12.8 g, 50 mM) in tetrahydrofuran (100 ml) is added dropwise and the mixture is stirred at room temperature for 2 hr. The mixture is filtered and the filtrate concentrated in vacuo. The concentrate is diluted with $H_2O$ and extracted with $CH_2Cl_2$. The extract is passed through a short column of silica gel to remove $Ph_3PO$ and the eluate is evaporated in vacuo to give methyl 1-acetoxy-6-methyl-2-methylene-5(E)-nonen-9-oic acid.

EXAMPLE 3

1-Hydroxy-6-methyl-2-methylene-5(E)-nonen-9-oic acid (9)

A solution of methyl 1-acetoxy-6-methyl-2-methylene-5-(E)-nonen-oic acid (2.5 g, 10 mM) in methanol (50 ml) is treated with 2 N NaOH—$H_2O$ (50 ml) while stirring at 0° C. under nitrogen. The cooling bath is removed after 1 hr, and the mixture is stirred at room temperature for 16 hr under nitrogen. The methanol is evaporated in vacuo and the residue is extracted with $CHCl_3$. The aqueous basic solution is cooled in an ice bath, and acidified with 2 N HCl—$H_2O$. It is extracted with $CHCl_3$, washed with 8% NaCl—$H_2O$, dried ($Na_2SO_4$) and evaporated in vacuo to give 1-hydroxy-6-methyl-2-methylene-5(E)-nonen-9-oic acid.

EXAMPLE 4

2,2-bis(Hydroxymethyl)-5-[2-(2-methyl-5-oxo-tetrahydrofuranyl)]tetrahydrofuran (10)

A. A solution of 1-hydroxy-6-methyl-2-methylene-5-(E)-nonen-9-oic acid (1.98 g, 10 mM) in acetone (100 ml) is cooled to −20° C. Potassium permanganate (3.2 g, 20 mM) in water (10 ml) is added while stirring at −20° C. Stirring at this temperature is continued for 1 hr. The $MnO_2$ is then filtered through Hy-flo and the acetone is evaporated in vacuo. The residue is dissolved in $CH_2Cl_2$ and purified through chromatography on silica gel to give a hydroxy acid which is dissolved in methanol (50 ml) containing conc. sulfuric acid (0.1 ml) and stirred at room temperature for 2 hr. The reaction mixture is cooled, treated with water (10 ml), concentrated in vacuo to remove the methanol and extracted with $CHCl_3$. The $CHCl_3$ extract is washed with 8% NaCl—$H_2O$, dried ($Na_2SO_4$) and evaporated in vacuo to give 2,2-bis(hydroxymethyl)-5-[2-(2-methyl-5-oxo-tetrahydrofuranyl]tetrahydrofuran.

B. A solution of methyl[2,5-cis-(2-acetoxymethyl-2-hydroxymethyltetrahydrofuran-5-yl)]-4-(4-hydroxypentanoate) (3.0 g, 10 mM) in methanol (100 ml) containing conc. sulfuric acid (0.2 ml) is stirred at room temperature for 16 hr. The reaction mixture is cooled, treated with water (20 ml), concentrated at vacuo to remove the methanol and extracted with $CHCl_3$. The extract is washed with 8% NaCl—$H_2O$, dried ($Na_2SO_4$) and evaporated in vacuo to give 2,2-bis(hydroxymethyl)-5-[2-(2-methyl-5-oxo-tetrahydrofuranyl)]tetrahydrofuran.

EXAMPLE 5

Methyl [2,5-cis-(2-acetoxymethyl-2-hydroxymethyltetrahydrofuran-5-yl)]-4-(4-hydroxypentanoate) (4)

A solution of methyl 1-acetoxy-6-methyl-2-methylene-5(E)-nonen-9-oic acid (4.8 g, 20 mM) in acetone (200 ml) is cooled to −20° C. Potassium permanganate (6.4 g, 40 mM) in water (20 ml) is added while stirring at −20° C. After stirring for 1 hr at −20° C., the $MnO_2$ is filtered through Hy-flo and the acetone is evaporated in vacuo. The residue is dissolved in $CHCl_3$ and purified by chromatography on silica gel to give methyl[2,5-cis-(2-acetoxymethyl-2-hydroxymethyltetrahydrofuran-5-yl)]-4-(4-hydroxypentanoate).

EXAMPLE 6

Methyl [2,5-cis-(2-acetoxymethyl)-2-(1,3-dioxolan-2-yl)tetrahydrofuran-5-yl]-4-(4-hydroxypentanoate) (5)

To anh. pyridine (8 ml) is added at 15° C., chromium trioxide (500 mg, 5 mM) in small portions over a period of 30 min with magnetic stirring. Stirring is continued at room temperature for 5 hr to obtain a uniform suspension. To this is added methyl[2,5-cis-(2-acetoxymethyl-2-hydroxymethyltetrahydrofuran-5-yl)]-4-(4-hydroxypentanoate) (1.52 g, 5 mM) in anh. pyridine (15 ml) within 5 min at 5° C. The mixture is then stirred at room temperature for 5 hr, acidified in the cold to pH 2.0 with 2 N HCl—$H_2O$ and extracted with ethyl acetate. The extract is filtered through Hy-flo, and evaporated in vacuo. The residue is dissolved in $CHCl_3$, washed with 8% NaCl—$H_2O$, dried ($Na_2SO_4$) and evaporated in vacuo to give the aldehydic precursor of the title compound. The aldehyde is treated with methyl ethyl ketone cyclic ethylene ketal (5.2 g, 4 mM) and p-toluenesulfonic acid monohydrate (0.16 g) in benzene (50 ml). The mixture is stirred and refluxed under nitrogen for 6 hr and then cooled in an ice bath. A saturated $NaHCO_3$ solution is added to neutralize the acid. The benzene layer is separated, washed with 8% NaCl—$H_2O$, dried ($Na_2SO_4$) and evaporated in vacuo to give methyl [2,5-cis-(2-acetoxymethyl)-2-(1,3-dioxolan-2-yl)tetrahydrofuran-5-yl]-4-(4-hydroxypentanoate).

EXAMPLE 7

[2,5-cis-(2-Bromomethyl)-2-(1,3-dioxolan-2-yl)tetrahydrofuran-5-yl]-4-(4-hydroxypentanoic acid) (6)

A mixture of methyl [2,5-cis-(2-acetoxymethyl)-2-(1,3-dioxolan-2-yl)tetrahydrofuran-5-yl]-4-(4-hydroxypentanoate) (1.0 g, 3 mM) in methanol (25 ml) is treated with 2 N NaOH—$H_2O$ (25 ml) while stirring at room temperature under nitrogen for 16 hr. The methanol is evaporated in vacuo, and the residue is extracted with $CHCl_3$. The aqueous basic solution is cooled in an ice bath, and acidified with 2 N HCl—$H_2O$. The acidic solution is extracted with $CHCl_3$, washed with 8% NaCl—$H_2O$, dried ($Na_2SO_4$) and evaporated in vacuo. The resulting crude dihydroxy acid is dissolved in carbon tetrabromide (3.0 g, 9 mM) and $CH_2Cl_2$ (10 ml). The solution is cooled to 0° C. under nitrogen and treated with triphenylphosphine (2.3 g, 9 mM). The resulting mixture is stirred for 2 hr and filtered through Hy-flo. The filtrate is then stirred with 5% aqueous $NaHCO_3$ to hydrolyze the acyl halide. The hydrolyze the acyl halide. The aqueous basic solution is then separated, cooled with an ice-H₂O mixture and acidified with 2N HCl-H₂O. The acidic solution is extracted with CHCl₃, washed with 8% NaCl-H₂O, dried (Na₂SO₄) and evaporated in vacuo to give [2,5-cis-(2-bromoethyl)-2-(1,3-dioxolan-2-yl)tetrahydrofuran-5-yl]-4-(hydroxypentanoic acid).

EXAMPLE 8

(1RS,4RS,5SR)-4-(2-Carboxyethyl)-1-(1,3-dioxolan-2-yl)-4-methyl-3,8-dioxabicyclo[3.2.1]octane (7)

A mixture of [2,5-cis-(2-bromomethyl)-2-(1,3-dioxlan-2-yl)tetrahydrofuran-5-yl]-4-(4-hydroxypentanoic acid) (1.0 g, 3 mM), anh. dimethylsulfoxide (8 ml) and KOH pellets (2 g, 37 mM) is stirred and heated at 45° C. under nitrogen for 3 days. It is then cooled to room temperature and CH₂Cl₂ (50 ml) and water (5 ml) are added. The organic layer is separated and is re-extracted with an ice-H₂O mixture. The aqueous basic solution is cooled with an ice-H₂O mixture, stirred and acidified with 2 N HCl—H₂O. The solution is extracted with CHCl₃ and the CHCl₃ extract is washed with 8% NaCl—H₂O solution, dried (Na₂SO₄) and evaporated in vacuo to give (1RS,4RS,5SR)-4-(2-carboxyethyl)-1-(1,3-dioxolan-2-yl)-4-methyl-3,8-dioxabicyclo[3.2.1]octane.

EXAMPLE 9

Methyl 1RS,4SR,5RS-4-(2-Carboxyethyl)-1-hydroxymethyl-4-methyl-3,8-dioxabicyclo[3.2.1]octane (11)

A solution of 2,2-bis-(hydroxymethyl)-5-[2-(2-methyl-5-oxo-tetrahydrofuranyl)]tetrahydrofuran (3.6 g, 15.6 mM) in methanol (40 ml) containing concentrated sulfuric acid (2.8 ml) is heated at 55° C. for 2 hr. The reaction mixture is cooled, treated with H₂O (10 ml), concentrated in vacuo to remove the methanol and extracted with CH₂Cl₂. The CH₂Cl₂ extract is washed with 8% NaCl—H₂O, dried (Na₂SO₄) and evaporated in vacuo to afford methyl 1RS,4SR,5RS-4-(2-carboxyethyl)-1-hydroxymethyl-4-methyl-3,8-dioxabicyclo[3.2.1]octane.

EXAMPLE 10

Methyl 1RS,4RS,5SR-4-(2-Carboxyethyl)-4-methyl-1-oxomethyl-3,8-dioxabicyclo[3.2.1]octane A solution of methyl 1RS,4SR,5RS-4-(2-carboxyethyl)-1-hydroxymethyl-4-methyl-3,8-dioxabicyclo[3.2.1]octane (1.6 g, 6.6 mM) in acetone (30 ml) at 0° C. under argon is treated with a slight excess of Jones reagent and stirred at that temperature for 10 min. The mixture is treated with methanol (2 ml), filtered through Hy-flo and concentrated in vacuo. The residue is treated with H₂O and extracted with CHCl₃. The CHCl₃ extract is washed with 8% NaCl—H₂O, dried (Na₂SO₄) and evaporated in vacuo to give methyl 1RS,4RS,5SR-4-(2-carboxyethyl)-4-methyl-1-oxomethyl-3,8-dioxabicyclo[3.2.1]octane.

EXAMPLE 11

Methyl 1RS,4RS,5SR-4-(2-Carboxyethyl)-1-(1,3-dioxolan-2-yl)-4-methyl-3,8-dioxabicyclo[3.2.1]octane A mixture of methyl 1RS,4RS,5SR-4-(2-carboxyethyl)-4-methyl-1-oxomethyl-3,8-dioxabicyclo[3.2.1]octane (1.3 g, 5.4 mM), p-toluenesulfonic acid monohydrate (45 mg), benzene (175 ml) and ethylene glycol (15 ml) is stirred and refluxed for 18 hr. The water formed during the reaction is removed by a Dean Stark trap fitted with a calcium carbide thimble. The mixture is cooled, diluted with H₂O and the benzene layer separated. The aqueous layer is extracted with additional benzene and the combined benzene extracts are washed with 8% NaCl—H₂O, dried (Na₂SO₄) and evaporated in vacuo to afford methyl 1RS,4RS,5SR-4-(2-carboxyethyl)-1-(1,3-dioxolan-2-yl)-4-methyl-3,8-dioxabicyclo[3.2.1]octane.

EXAMPLE 12

1RS,4RS,5SR-4-(2-Carboxyethyl)-1-(1,3-dioxolan-2-yl)-4-methyl-3,8-dioxabicyclo[3.2.1]octane (7)

A mixture of methyl 1RS,4RS,5SR-4-(2-carboxyethyl)-1-(1,-3-dioxolan-2-yl)-4-methyl-3,8-dioxabicyclo[3.2.1]octane (1.3 g, 4.5 mM), methanol (20 ml) and 2 N NaOH (5 ml) is stirred at room temperature for 18 hr. The reaction mixture is diluted with H₂O (30 ml), concentrated in vacuo, cooled and acidified with 2 N HCl—H₂O. The acidic layer is extracted with CHCl₃ and the CHCl₃ extract is washed with 8% NaCl—H₂O, dried (Na₂SO₄) and evaporated in vacuo to give 1RS,4RS,5SR-4-(2-carboxyethyl)-1-(1,3-dioxolan-2-yl)-4-methyl-3,8-dioxabicyclo[3.2.1]octane.

EXAMPLE 13

1RS,4RS,5SR-1-(1,3-Dioxolan-2-yl)-4-(3-hydroxypropyl)-4-methyl-3,8-dioxabicyclo[3.2.1]octane A. A 1 molar BH₃ tetrahydrofuran solution (5 ml) is added during a 5 min period to a stirred solution of 1RS,4RS,5SR-4-(2-carboxyethyl)-1-(1,3-dioxolan-2-yl)-4-methyl-3,8-dioxabicyclo[3.2.1]octane (785 mg, 2.8 mM) in anh. tetrahydrofuran (10 ml) at 0° C. under nitrogen. The mixture is stirred at 0° C. for 15 min and then at room temperature for 1.5 hr. The reaction mixture is then added cautiously to ice water (10 ml) and extracted with CHCl₃. The extract is washed with dilute NaHCO₃ solution, dried (Na₂SO₄) and evaporated in vacuo to give 1RS,4RS,5SR-1(1,3-dioxolan-2-yl)-4-(3-hydroxypropyl)-4-methyl-3,8-dioxabicyclo[3.2.1]octane.

B. A solution of 1RS,4RS,5SR-1-(1,3-dioxolan-2-yl)-4-methyl-4-[3-tetrahydropyran-2-yloxy)propyl]-3,8-dioxabicyclo[3.2.1]octane (2.7 g, 7.9 mM) in methanol (25 ml) containing 1 N HCL (4.9 ml) is stirred at room temperature for 2.5 hr. The reaction mixture is concentrated in vacuo, diluted with H₂O and extracted with CHCl₃. The CHCl₃ extract is washed with 8% NaCl—H₂O, dried (Na₂SO₄) and evaporated in vacuo to give 1RS,4RS,5SR-1-(1,3-dioxolan-2-yl)-4-(3-hydroxypropyl)-4-methyl-3,8-dioxabicyclo[3.2.1]octane.

EXAMPLE 14

1RS,4RS,5SR-1-(1,3-Dioxolan-2-yl)-4-(3-methanesulfonyloxypropyl)-4-methyl-3,8-dioxabicyclo[3.2.1]octane (8)

A mixture of 1RS,4RS,5SR-1-(1,3-dioxolan-2-yl)-4-(3-hydroxypropyl)-4-methyl-3,8-dioxabicyclo[3.2.1]octane (1.4 g, 5.4 mM), triethylamine (1.63 ml) and CH₂Cl₂ (15 ml) cooled to 0° C. and stirred under nitrogen is treated dropwise with methanesulfonyl chloride (0.93 g, 8 mM). The reaction mixture is stirred at 0° C. for 5 hr and then added to ice water. The CH₂Cl₂ layer is separated and the aqueous portion extracted with additional CH₂Cl₂. The combined CH₂Cl₂ extracts are washed with 0.5 N HCl—H₂O and 8% NaCl—H₂O, dried (Na₂SO₄) and evaporated in vacuo to afford 1RS,4RS,5SR-1-(1,3-dioxolan-2-yl)-4-(3-methanesulfonyloxypropyl)-4-methyl-3,8-dioxabicyclo[3.2.1]octane.

EXAMPLE 15

2,2-bis(Bromomethyl)-5-[2-(2-methyl-5-oxo-tetrahydrofuranyl)]tetrahydrofuran

A mixture of 2,2-bis(hydroxymethyl)-5-[2-(2-methyl-5-oxo-tetrahydrofuranyl)]tetrahydrofuran (3.1 g, 13.5 mM) and carbon tetrabromide (9.0 g, 27.2 mM) in CH₂Cl₂ (25 ml) is cooled to 0° C. under a nitrogen atmosphere and treated with triphenylphosphine (7.83 g, 29.9 mM). The mixture is stirred for 2 hr, filtered and washed with water. The organic layer is dried (Na₂SO₄) and evaporated in vacuo to afford 2,2-bis(bromomethyl)-5-[2-(2-methyl-5-oxo-tetrahydrofuranyl)]tetrahydrofuran.

EXAMPLE 16

1RS,4RS,5SR-1-Bromomethyl-4-(2-carboxyethyl)-4-methyl-3,8-dioxabicyclo[3.2.1]octane (12)

A. A mixture of 2,2-bis(bromomethyl)-5-[2-(2-methyl-5-oxo-tetrahydrofuranyl)]tetrahydrofuran (2.3 g, 6.5 mM) and KOH (4 g) in dimethylsulfoxide (25 ml) is heated at 60° C. for 28 hr under nitrogen. The reaction mixture is poured into cold 8% NaCl—H₂O and extracted with CH₂Cl₂ to remove neutral impurities. The aqueous solution is acidified with 6 N HCl—H₂O and extracted with CH₂Cl₂. The CH₂Cl₂ extract is washed with 8% NaCl—H₂O, dried (Na₂SO₄) and evaporated in vacuo to afford 1RS,4RS,5SR-1-bromomethyl-4-(2-carboxyethyl)-4-methyl-3,8-dioxabicyclo[3.2.1]-octane.

B. Following the procedures of examples 15 and 12, but substituting the compound of example 9 for 2,2-bis(bromomethyl)-5-[2-(2-methyl-5-oxo-tetrahydrofuranyl)]tetrahydrofuran, there is obtained 1RS,4RS,5SR-1-bromomethyl-4-(2-carboxyethyl)-4-methyl-3,8-dioxabicyclo[3.2.1.]octane.

EXAMPLE 17

1RS,4RS,5SR-1-Bromomethyl-4-(3-hydroxypropyl)-4-methyl-3,8-dioxabicyclo[3.2.1]octane Following the procedure of example 13A, but substituting the compound of example 16 for 1RS,4RS,5SR-4-(2-carboxyethyl)-1-(1,3-dioxolan-2-yl)-4-methyl-3,8-dioxabicyclo[3.2.1]octane, there is obtained 1RS,4RS,5SR-1-bromomethyl-4-(3-hydroxypropyl)-4-methyl-3,8-dioxabicyclo[3.2.1]octane.

EXAMPLE 18

1RS,4RS,5SR-1-Bromomethyl-4-methyl-4-[3-(tetrahydropyran-2-yloxy)propyl]-3,8-dioxabicyclo[3.2.1]octane (13)

A solution of 1RS,4RS,5SR-1-bromomethyl-4-(3-hydroxypropyl)-4-methyl-3,8-dioxabicyclo[3.2.1]octane (3.2 g, 11.5 m), dihydropyran (0.97 g, 11.5 mM) and p-toluenesulfonic acid monohydrate (40 mg) in ether (50 ml) is stirred at room temperature overnight under nitrogen. The reaction mixture is washed with dilute NaHCO₃ solution, 8% NaCl—H₂O, dried (Na₂SO₄) and evaporated in vacuo to afford 1RS,4RS,5SR-1-bromomethyl-4-methyl-4-[3-(tetrahydropyran-2-yloxy)propyl]-3,8-dioxabicyclo[3.2.1]octane.

EXAMPLE 19

1RS,4RS,5SR-4-Methyl-1-oxomethyl-4-[3-(tetrahydropyran-2-yloxy)propyl]-3,8-dioxabicyclo[3.2.1]octane A mixture of 1RS,4RS,5SR-1-bromomethyl-4-methyl-4-[3-(tetrahydropyran-2-yloxy)propyl]-3,8-dioxabicyclo[3.2.1]octane (1.2 g, 3.3 mM) in dimethylsulfoxide (10 ml) containing silver perchlorate (400 mg) is stirred at room temperature for 40 hr. The reaction mixture is poured into H₂O and extracted with CH₂Cl₂. The CH₂Cl₂ extract is washed with 8% NaCl—H₂O, dried (Na₂SO₄) and evaporated in vacuo to give 1RS,4RS,5SR-4-methyl-1-oxomethyl-4-[3-(tetrahydropyran-2-yloxy)propyl]-3,8-dioxabicyclo[3.1.1]octane.

EXAMPLE 20

1RS,4RS,5SR-1-(1,3-Dioxolan-2-yl)-4-methyl-4-[3-tetrahydropyran-1-yloxy)propyl]-3,8-dioxabicyclo[3.2.1]octane Following the procedure of example 11, but substituting the compound of example 19 for methyl 1RS,4RS,5SR-4-(2-carboxyethyl)-4-methyl-1-oxomethyl-3,8-dioxabicyclo[3.2.1]octane, there is obtained 1RS,4RS,5SR-1-(1,3-dioxolan-2-yl)-4-[3-tetrahydropyran-2-yloxy)propyl]-3,8-dioxabicyclo[3.2.1]octane.

EXAMPLE 21

1RS,4RS,5SR-4-(4-Carboxypentyl)-1-(1,3-dioxolan-2-yl)-4-methyl-3,8-dioxabicyclo[3.2.1]octane (14)

A solution of 1RS,4RS,5SR-1-(1,3-dioxolan-2-yl)-(3-methanesulfonyloxypropyl)-4-methyl-3,8-dioxabicyclo[3.2.1]octane (840 mg, 2.5 mM) in tetrahydrofuran (15 ml) is slowly added to methyl-2-lithio-propionate (6 mM) in tetrahydrofuran (15 ml) maintained at −78° C. under nitrogen. The reaction mixture is stirred for 2 hr at −78° C., allowed to warm to room temperature and stirred for an additional 45 min after which it is poured into saturated NH₄Cl—H₂O and extracted with CH₂Cl₂. The CH₂Cl₂ extract is washed with 8% NaCl—H₂O, dried (Na₂SO₄) and evaporated in vacuo to give the ester. Hydrolysis of the ester as described in example 3 affords 1RS,4RS,5SR-4-(4-carboxypentyl)-1-(1,3-dioxolan-2-yl)-4-methyl-3,8-dioxabicyclo[3.2.1]octane.

EXAMPLE 22

1RS,4RS,5SR-4-(4,8-Dimethyl-5-oxo-7-nonenyl-1-(1,3-dioxolan-2-yl)-4-methyl-3,8-dioxabicyclo[3.2.1]octane A mixture of 1RS,4RS,5SR-4-(4-carboxypentyl)-1-(1,3-dioxolan-2yl)-4-methyl-3,8-dioxabicyclo[3.2.1]octane (753 mg, 2.4 mM), lithium hydride (96 mg, 12 mM) and ether (20 ml) is stirred at room temperature under nitrogen for 1.5 hr. The reaction mixture is treated with an excess of 3-methyl-2-butenyl lithium, stirred at room temperature for 2 hr, and then treated with dilute NaHCO₃ solution. The ether layer is separated and the aqueous layer is extracted with CHCl₃. The combined organic fractions are washed with 8% NaCl—H₂O, dried (Na₂SO₄) and evaporated in vacuo to afford 1RS,4RS,5SR-4-(4,8-dimethyl-5-oxo-7-nonenyl)-1-(1,3-dioxolan-2-yl)-4-methyl-3,8-dioxabicyclo[3.2.1]octane.

EXAMPLE 23

1RS,4RS,5SR-4-(4,8-Dimethyl-5-hydroxy-7-nonenyl)-1-(1,3-dioxolan-2-yl)-4-methyl-3,8-dioxabicyclo[3.2.1]octane A solution of 1RS,4RS,5SR-4-(4,8-dimethyl-5-oxo-7-nonenyl)1-(1,3-dioxolan-2-yl)-4-methyl-3,8-dioxabicyclo[3.2.1]octane (1.2 g, 3.3 mM) in methanol (50 ml) is treated at 0° C. with sodium borohydride (300 mg) and stirred at ambient temperature for 1 hr. Acetone (1 ml) is added and the reaction is stirred for 30 min. The reaction mixture is treated with $H_2O$, concentrated in vacuo, and extracted with $CHCl_3$. The $CHCl_3$ extract is washed with 8% $NaCl$—$H_2O$, dried ($Na_2SO_4$) and evaporated in vacuo to afford 1RS,4RS,5SR-4-(4,8-dimethyl-5-hydroxy-7-nonenyl)-1-(1,3-dioxolan-2-yl)-4-methyl-3,8-dioxabicyclo[3.2.1]octane.

EXAMPLE 24

1RS,4RS,5SR-4-(4,8-Dimethyl-5-hydroxy-7-nonenyl)-4-methyl-1-oxomethyl-3,8-dioxabicyclo[3.2.1]octane A solution of 1RS,4RS,5SR-4-(4,8-dimethyl-5-hydroxy-7-nonenyl)-1-(1,3-dioxolan-2-yl)-4-methyl-3,8-dioxabicyclo[3.2.1]octane (627 mg, 1.7 mM) in acetone (10 ml) containing 1 N HCL (0.9 ml) is stirred at room temperature for 18 hr. The mixture is concentrated in vacuo, diluted with $H_2O$, extracted with $CHCl_3$ and the $CHCl_3$ extract is washed with 8% $NaCl$—$H_2O$, dried ($Na_2SO_4$) and evaporated in vacuo to give 1RS,4RS,5SR-4-(4,8-dimethyl-5-hydroxy-7-nonenyl)-4-methyl-1-oxomethyl-3,8-dioxabicyclo[3.2.1]octane.

EXAMPLE 25

1RS,4RS,5S,-4-(5-Acetoxy-4,8-dimethyl-7-nonenyl)-4-methyl-1-oxomethyl-3,8-dioxabicyclo[3.2.1]octane (15)

A solution of 1RS,4RS,5SR-4-(4,8-dimethyl-5-hydroxy-7-nonenyl)-4-methyl-1-oxomethyl-3,8-dioxabicyclo[3.2.1]octane (512 mg, 1.6 mM) in acetic anhydride (1 ml) and pyridine (2 ml) is stirred at room temperature for 4 hr. The mixture is diluted with $H_2O$, and extracted with $CHCl_3$ and, the $CHCl_3$ extract is washed with 8% $NaCl$—$H_2O$, dried ($Na_2SO_4$) and evaporated in vacuo to give 1RS,4RS,5Sr-4-(5-acetoxy-4,8-dimethyl-7-nonenyl)-4-methyl-1-oxomethyl-3,8-dioxabicyclo[3.2.1]octane.

EXAMPLE 26

1RS,4RS,5SR-4-(5-Acetoxy-4,8-dimethyl-7-nonenyl)-4-methyl-1-vinyl-3,8-dioxabicyclo[3.2.1]octane A suspension of methyltriphenylphosphonium bromide (2.15 g, 6 mM) in tetrahydrofuran (20 ml) at 0° C. is treated with n-butyllithium (3 ml, 6 mM) and stirred for 1 hr at 0° C. to generate the ylide. A solution of 1RS,4RS,5SR-4-(5-acetoxy-4,8-dimethyl-7-nonenyl)-4-methyl-1-oxomethyl-3,8-dioxabicyclo[3.2.1]octane (2.01 g, 5.5 mM) in tetrahydrofuran (10 ml) is added dropwise and the mixture is stirred at room temperature for 2 hr. The mixture is filtered, and the filtrate is concentrated in vacuo and diluted with $H_2O$. The aqueous layer is extracted with $CH_2Cl_2$, and the extracts are washed with 8% $NaCl$—$H_2O$, dried ($Na_2SO_4$) and evaporated in vacuo to give 1RS,4RS,5SR-4-(5-acetoxy-4,8-dimethyl-7-nonenyl)-4-methyl-1-vinyl-3,8-dioxabicyclo[3.2.1]octane.

EXAMPLE 27

1RS,4SR,5RS-4-(5-Acetoxy-4,8-dimethyl-7-nonenyl)-1-(2-hydroxyethyl)-4-methyl-3,8-dioxabicyclo[3.2.1]octane A solution of 1RS,4RS,5SR-4-(5-acetoxy-4,8-dimethyl-7-nonenyl)-4-methyl-1-vinyl-3,8-dioxabicyclo[3.2.1]octane (426 mg, 1.2 mM) in tetrahydrofuran (10 ml) at 0° C. under nitrogen is treated with a 1 M $BH_3$.tetrahydrofuran solution (1.2 ml). The reaction mixture is stirred at 0° C. for 30 min, warmed to room temperature and stirred for 3 hr. The mixture is cooled to 0° C. and treated with 3 N NaOH (0.3 ml) followed by 30% hydrogen peroxide (0.3 ml). The reaction mixture is allowed to reach room temperature and is stirred at room temperature for 3 hr, after which it is diluted with water and extracted with $CH_2Cl_2$. The $CH_2Cl_2$ extract is washed with 8% $NaCl$—$H_2O$, dried ($Na_2SO_4$) and evaporated in vacuo to give 1RS,4SR,5RS-4-(5-acetoxy-4,8-dimethyl-7-nonenyl)-1-(2-hydroxyethyl)-4-methyl-3,8-dioxabicyclo[3.2.1]octane.

EXAMPLE 28

1RS,4SR,5RS-4-(5-Acetoxy-4,8-dimethyl-7-nonenyl)-4-methyl-3,8-dioxabicyclo[3.2.1]octane-1-acetic acid A solution of 1RS,4SR,5RS-4-(5-acetoxy-4,8-dimethyl-7-nonenyl)-1-(2-hydroxyethyl)-4-methyl-3,8-dioxabicyclo[3.2.1]octane (229 mg, 0.6 mM) in acetone (10 ml) at 5° C. under argon is treated with excess Jones reagent and stirred for 30 minutes. The mixture is treated with methanol (1 ml), filtered through Hy-flo and concentrated in vacuo. The residue is treated with $H_2O$ and extracted with $CHCl_3$. The $CHCl_3$ fraction is extracted with 0.5 N NaOH. The basic extract is acidified with 0.5 N $HCl$—$H_2O$ and extracted with $CHCl_3$. The $CHCl_3$ extract is dried ($Na_2SO_4$) and evaporated in vacuo to give 1RS,4SR,5RS-4-(5-acetoxy-4,8-dimethyl-7-nonenyl)-4-methyl-3,8-dioxabicyclo[3.2.1]octane-1-acetic acid.

EXAMPLE 29

1RS,4SR,5RS-4-(4,8-Dimethyl-5-hydroxy-7-nonenyl)-4-methyl-3,8-dioxabicyclo[3.2.1]octane-1-acetic acid Following the procedure of example 12, but substituting the compound of example 28 for methyl 1RS,4SR,5RS-4-(2-carboxyethyl)-1-(1,3-dioxolan-2-yl)-4-methyl-3,8-dioxabicyclo[3.2.1]octane, there is obtained 1RS,4SR,5RS-4-(4,8-dimethyl-5-hydroxy-7-nonenyl)-4-methyl-3,8-dioxabicyclo[3.2.1]octane-1-acetic acid nmr ($CDCl_3$)δ0.88 (d, $\underline{CH_3}CH$), 1.31 (s, $C_4$—$CH_3$), 1.63 and 1.71 (br s, $(CH_3)_2C=C$), 2.60 (s, —$\underline{CH_2}CO_2H$), ms, M+498, bis-trimethylsilyl derivative.

PREPARATION OF STARTING MATERIAL

EXAMPLE A

1-Bromo-6-methyl-2-oxo-5(E)-nonen-9-al

Periodic acid (34.6 g, 3×0.051 M) dissolved in aqueous tetrahydrofuran (240 ml, 5% by volume) is added to crude 1-bromo-6,10-dimethyl-9,10-oxido-5(E)-undecen-2-one (14.7 g, 0.051 M) in aqueous tetrahydrofuran (240 ml,, 5% by volume) while stirring at 20° C. over a 3 minute period and the mixture is stirred at 20° C. for an additional 9 minutes. The reaction mixture is then added to a stirred mixture of ice cold saturated $NaHCO_3$—$H_2O$ (400 ml) and ether (700 ml). The mixture is filtered, the organic layer is separated, washed with 10% NaHCO₃—H₂O, NaCl—H₂O, dried with Na₂SO₄, filtered and concentrated in vacuo to give crude 1-bromo-6-methyl-2-oxo-5(E)-nonen-9-al (14.5 g).

TLC (10% ether in CH₂Cl₂): $R_f$=0.52 IR (neat): 2730 (CH of aldehyde), 1706 cm⁻¹ (broad CO groups).

The crude reaction product is used without further purification in the next step.

EXAMPLE B

1-Bromo-6-methyl-2-oxo-5(E)-nonen-9-oic acid

Jones reagent (20 ml) is added to 1-bromo-6-methyl-2-oxo-5(E)-nonen-9-al (14.5 g, 0.059 M of ~38% pure) in acetone (250 ml) within 5 minutes while stirring at 0° C. The resultant solution is stirred for an additional 10 minutes at 0° C. and then added to a stirred solution of ice cold saturated NaHCO₃—H₂O (350 ml). The acetone is removed in vacuo, CH₂Cl₂ (300 ml) is added, and the mixture is filtered. The organic phase is washed with H₂O and then added to the NaHCO₃—H₂O. The aqueous basic solution is washed once with CH₂Cl₂ and once with ether, stirred at 0° C. and acidified carefully with ice cold 6 N HCl—H₂O to pH=2.0. The acidic solution is then extracted twice with CH₂Cl₂ and once with ether. The extracts are washed separately with NaCl—H₂O, combined, dried with Na₂SO₄, filtered, and evaporated in vacuo to give 1-bromo-6-methyl-2-oxo-5(E)-nonen-9-oic acid (3.92 g, 29.3%). The compound solidifies on standing.

TLC (Et₂O): $R_f$=0.67; IR (neat)- 2700–2330 (OH), 1710 cm⁻¹ (CO). NMR (CDCl₃,δ): 8.67 (br, 1H, —CO₂H), 5.17 (t, 1H, vinylic H), 3.88 (s, 2H, —CO—CH₂—Br), 1.67 (br. s, 3H, vinylic CH₃).

We claim:

1. The process for the preparation of a compound of the formula

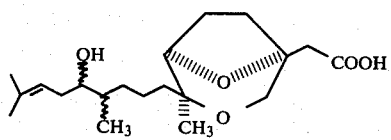

which comprises reacting a compound of the formula

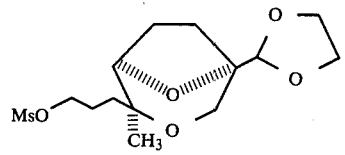

with methyl 2-lithio-propionate and hydrolyzing the ester to form a compound of the formula

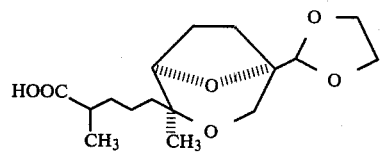

reacting the acid with 3-methyl-2-butenyl lithium, reacting the ketone formed with a reducing agent, treating the product formed with aqueous hydrochloric acid and esterifying the hydroxy compound with an esterifying agent to form a compound of the formula

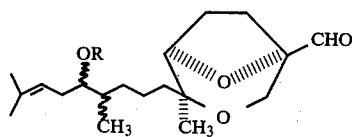

reacting the aldehyde with a compound of the formula

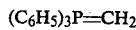

(C₆H₅)₃P═CH₂ reacting the product formed first with borane-THF followed by treatment with an alkali metal hydroxide and hydrogen peroxide, oxidizing the product formed with an oxidizing agent, hydrolyzing the ester with a base and treating the product formed with a mineral acid, wherein R is a lower alkanoyl group having 2-6 carbon atoms and Ms is a mesyl group.

2. The process of claim 1 wherein the reducing agent is sodium borohydride.

3. The process of claim 1 wherein the esterifying agent is acetic anhydride.

4. The process of claim 1 wherein the alkali metal hydroxide is sodium hydroxide.

5. The process of claim 1 wherein the oxidizing agent is Jones reagent.

6. The process of claim 1 wherein the hydrolyzing base is sodium hydroxide and the mineral acid is hydrochloric acid.

7. The process of claim 1 wherein R is acetyl.

* * * * *